United States Patent [19]
Chan

[11] Patent Number: 6,030,555
[45] Date of Patent: Feb. 29, 2000

[54] PHOTOCHROMIC SPIROXAZINES, COMPOSITIONS AND ARTICLES CONTAINING THEM

[75] Inventor: You-Ping Chan, Lyons, France

[73] Assignee: Corning Incorporated, Corning, N.Y.

[21] Appl. No.: 09/000,370

[22] PCT Filed: Jul. 22, 1996

[86] PCT No.: PCT/US96/12083

§ 371 Date: Jan. 28, 1998

§ 102(e) Date: Jan. 28, 1998

[87] PCT Pub. No.: WO97/08573

PCT Pub. Date: Mar. 6, 1997

[30] Foreign Application Priority Data

Aug. 30, 1995 [FR] France .................................. 95 10221

[51] Int. Cl.[7] .............................. G02B 5/23; C07D 265/00
[52] U.S. Cl. ........................... 252/586; 544/71; 523/106; 525/66
[58] Field of Search .............................. 252/586; 544/71; 523/106; 525/66

[56] References Cited

U.S. PATENT DOCUMENTS

| | | | |
|---|---|---|---|
| 4,913,544 | 4/1990 | Rickwood et al. | 252/586 |
| 4,962,013 | 10/1990 | Tateoka et al. | 252/586 |
| 5,114,621 | 5/1992 | Gugliemetti et al. | 252/586 |
| 5,139,707 | 8/1992 | Gugliemetti et al. | 252/586 |
| 5,446,151 | 8/1995 | Rickwood et al. | 544/71 |
| 5,529,725 | 6/1996 | Gugliemetti et al. | 252/586 |

*Primary Examiner*—Philip Tucker
*Attorney, Agent, or Firm*—Angela N. Nwaneri; Peter Rogalskyj

[57] ABSTRACT

The invention concerns photochromic compounds having a formula (I), where $R^1$ is a polycyclo group formed by at least one alicyclic group linked to, bridged or condensed, with at least one other aliphatic or aromatic ring.

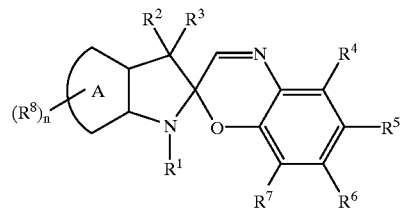

(I)

44 Claims, No Drawings

PHOTOCHROMIC SPIROXAZINES, COMPOSITIONS AND ARTICLES CONTAINING THEM

The present invention concerns novel compounds of the spiroxazine type presenting, in particular, photochromic properties. It also concerns the photochromic compositions and ophthalmic articles (e.g., lenses) which contain spiroxazines.

The photochromic compounds are capable of changing color due to the influence of a poly- or monochromatic light (e.g., UV) and they are capable of recovering their initial color when the irradiation with light stops, or due to the influence of a poly- or monochromatic light which is different from the first light, or due to the influence of temperature and/or of a poly- or monochromatic light which is different from the first one.

These photochromic compounds are applied in various fields, for example, for the manufacture of ophthalmic lenses, contact lenses, some sunshades, filters, optics for cameras or photographic apparatus or other optical and observation devices, glass partitions, decorative objects, display elements or for the storage of information by optical inscription (coding).

In the filed of ophthalmic optics, and in particular in the field of eyeglasses, a photochromic lens, comprising one or more photochromic compounds, must present:

- a high transmission in darkness or in the absence of sunlight,
- a low transmission (high colorability) when exposed to irradiation by sunlight,
- an appropriate kinetics of coloration and decoloration,
- a tint which is acceptable to the consumer (gray or chestnut brown, preferably), with, preferably, maintenance of the selected tint during the course of the coloration and the decoloration of the lens,
- a maintenance of the performances of the characteristics in a temperature range of 0–40° C.,
- a significant durability, because the objectives intended are sophisticated, and therefore expensive, corrective lenses.

These lens characteristics are in fact determined by the active photochromic compounds which, in addition, must be perfectly compatible with the organic or mineral support which constitutes the lens.

Moreover, it should be noted that the obtention of a gray or chestnut brown tint may require the use of at least two photochromes of different colors, that is, having distinct maximum absorption wavelengths in the visible range ($\lambda_{max}$). This association thus imposes still other requirements on photochromic compounds. In particular, the kinetics of coloration and decoloration of the two or more associated active photochromic compounds must be essentially identical. The same applies to their stability over time and, also, to their compatibility with a plastic or mineral support.

Among the numerous photochromic compounds described in the prior art, one can cite the indolinospironaphtoxazines described in U.S. Pat. Nos. 3,578,602; 3,562,172; 4,215,010; European Patent Nos. 0,171,909; 0,313,941; French Patent No. 2,647,789 and European Patent No. 0,600,669:

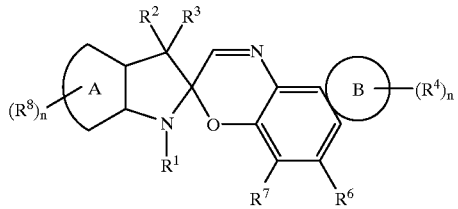

The group $R_1$ of these molecules represent straight or branched alkyls, alkylaryls or alicyclics. These compounds are considered to meet the specifications defined above.

In fact, while these compounds have indeed one or more of the basic properties sought, such as a high transmission in darkness, a high colorability when exposed to sun radiation, absorption in the blue or violet (570–630 nm), a rapid kinetics of coloration and decoloration, all the compounds described to this day do not have the complete combination of the wanted properties which is required for the production of satisfactory articles which can be manufactured industrially.

Whereas the prior art teach how to modify the absorption band by the addition of substituents to the different positions of the rings and, also, teach how to modify the kinetics of decoloration, in contrast, it does not teach how to increase the colorability of these molecules without increasing the residual coloration in the inactivated state and, above all, on how to make them photochemically stable so as to allow their use on an industrial scale. Indeed, without a high stability, these expensive molecules, introduced into a sophisticated lens, cannot be used.

It is the merit of the applicant to have found, unexpectedly, that the presence of polycyclic groups, preferably bicycloalkyl groups, allowed a solution of the problem of the stability, the residual coloration and the colorability, which are essential for the above-mentioned applications.

The originality of the invention resides in the surprising effect of the polycyclic groups, which increases the colorability of the spiroxazines without increasing their residual coloration, while ensuring excellent photostability.

Thus, the present invention concerns a compound, in particular a photochromic compound, having the following general formula (I):

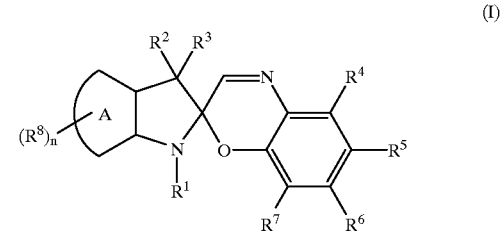

in which, $R^1$ is a polycyclic group formed by at least one alicyclic group which is linked to bridged or condensed with at least one other aliphatic and/or aromatic ring, where the rings can optionally contain at least one heteroatom and at least one unsaturation, $R^2$, $R^3$ are identical or different and they represent an alkyl group, straight or branched, of 1–12 carbon atoms, an alkenyl group, alkynyl, aryl, alkylaryl, cycloalkyl, $R^2$ and $R^3$ can, optionally, combine to form a carbocyclic or heterocyclic group having 5 to 10 atoms, $R^4$, $R^5$, $R^6$ and $R^7$ are identical or different and they represent:

hydrogen, an alkyl, cycloalkyl, alkenyl, alkynyl, aryl (preferably phenyl, naphthyl mono-, -di-, or trisubstituted by electron done or acceptor groups), heteroaryl, aryloxy or aralkyl, said group being optionally halogenated, a halogen, preferably F, Br, Cl, OR, SR, —OCOR-, —COOR, with R=H, alkyl and/or cycloaklyl and/or aryl, a (poly)ether, a (poly)amide, a (poly)carbonate, a (poly) carbamate, a (poly)urea or a (poly)ester,

* an amino radical which gives rise, once it is bound in (I), to a primary, secondary or tertiary amine, said amine being alkyl, aryl or aralkyl, mono- or disubstituted depending on its nature,

* or an aminocyclic radical containing, optionally, one or more heteroatoms, or an electron withdrawing group selected, preferably, from the group comprising $CF_3$, CN, $NO_2$, SCN, where at least two of the radicals $R^4$, $R^5$, $R^6$, $R^7$, preferably carried by two adjacent carbon atoms, can combine to form at least one aromatic ring having 5 or 6 members or an aliphatic ring having 5 to 7 members, advantageously 5 or 6 members, said ring(s) comprising, optionally, at least one heteroatom, so as to form at least one heterocyclic ring, the latter being optionally substituted by one or more radicals which may be identical or different, and have the same definition as given above for $R^4$ to $R^7$, A represents a (hetero)aromatic ring (containing, for example, at least one nitrogen atom) and possibly substituted by one or more radicals $R^8$, which may be identical or different, and having the same definition as given above for $R^4$ to $R^7$, n is a whole number and when n≧2, two of the radicals $R^8$ can possibly combine to form at least one aromatic or heteroaromatic ring.

Preferably, $R^1$ represents a bicyclic group. It is particularly preferred for $R^1$ to represent an asymmetric bicyclic group. The asymmetry can be the result of either the nature of the group or the present of a substituent(s). Preferred examples of such asymmetric bicyclic groups are substituted or unsubstituted norbornyl groups.

According to the invention it is possible to consider the substitution of at least one of the rings of $R^1$ by at least one substituent $R^9$ which has the same definition as that given above for $R^4$ to $R^7$.

Specific examples of groups $R^1$ are the following:

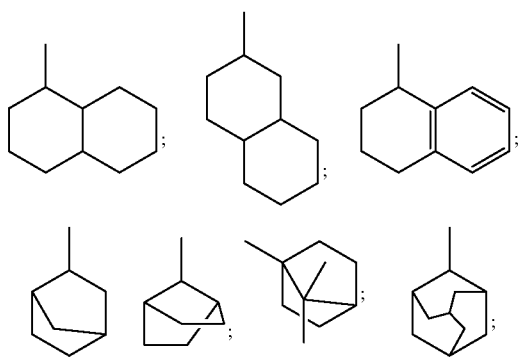

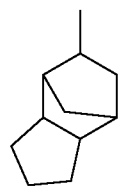

among many others.

Preferred compounds of the invention have the following formula (I'):

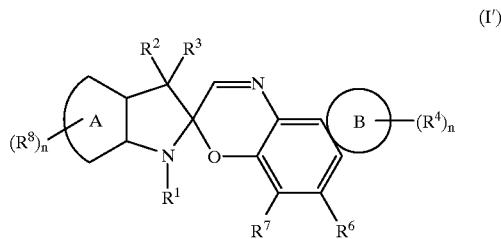

(I')

where A, and $R^1$ to $R^7$ are as defined above, and B is an aromatic or aliphatic ring having 5 to 7 members, optionally comprising a heteroatom which may or may not be substituted by one or more radicals which may be identical or different, and have the same definition as given for $R^4$ to $R^7$.

According to a particularly preferred embodiment of the invention, ring A is a phenyl group and $R^4$ and $R^5$ combine to form an annealed aromatic ring or a bicyclic aromatic ring condensed with the phenyl group which bears them. This corresponds to the following formula (I"):

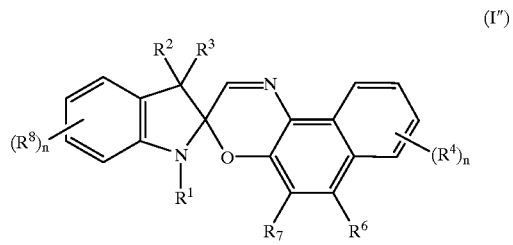

(I")

in which $R^1$ to $R^4$ and $R^6$ and $R^8$ are as defined above, and n and m assume the values 0 to 4.

Among the substituents which can be considered for the compounds with formula (I), (I') and (I") according to the invention, groups $R^4$ and $R^9$ must be considered, which comprise and/or form at least one reactive function for polymerization and/or crosslinking, selected, preferably, from the following list: alkenyl, advantageously vinyl, methacryloyl, acryloyl, acryloxyalkyl, methacryloxyalkyl or epoxy.

Thus, the photochromic compounds according to the invention can be designed as monomers, of different types or not, which can react between themselves or with other comonomers, to form homopolymers and/or copolymers which carry a photochromic functionality and which have the mechanical properties of macromolecules. It follows that one of the objects of the present, invention are formed by these homopolymers or copolymers comprised of the (co) monomers and/or by the crosslinkages, at least in part made up of photochromic compounds (I), (I') and (I") according to the invention.

In the same order of ideas, the above-mentioned compounds (I), (I') and (I") can be considered to be crosslinking agents which have reactive functions capable of allowing the formation of bridges between polymer chains of photochromic nature of not. The crosslinked compounds which can thus be obtained, also constitute another object of the present invention.

In a general manner, in the preceding formulas, the following designations are used, according to the invention:

"alkyl," referring preferably to a straight or branched hydrocarbon group having from 1 to 12 carbon atoms;

"alkoxyl," referring to a group of O-alkyl type preferably having from 1 to 10 carbon atoms, "aryl," referring to an aromatic hydrocarbon group containing at least 6 carbon atoms, "heteroaryl," referring to an aromatic hydrocarbon group comprising at least 5 atoms, of which at least one is a heteroatom, "aralkyl," a group comprising at least one alkyl and at least one aryl, as defined above, "heteroatom," atoms different from C and H, belonging preferably to the following group: N, O, S and P.

The photochromic compounds which are used particularly preferentially in the context of the invention thus are, as can be concluded from the above, indolinospironaphthoxazines or indolinospirobenzoxazines.

The most advantageous indolinospiroxazines include those having the formula:

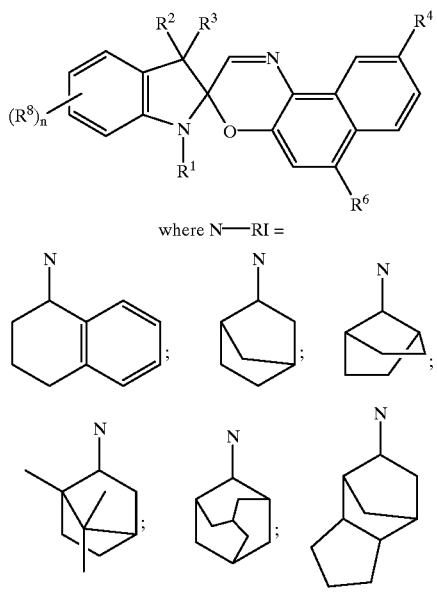

n=0, 1 or 2 and $R^2$, $R^3 = C_1-C_5$ alkyl, $R^4$=H, OMe, $R^6$=H, OMe or amino, $R^8$=H, Me, OMe or $CF_3$.

It is the merit of the applicant to have disclosed these compounds, because they present particularly advantageous photochromic properties. More specifically, they have a high colorability, particularly in the blue region. They are thus well suited to combination, observing compatibility and complementarity requirements, with photochromes which absorb in the yellow, orange, red and violet, so as to obtain a broad coverage of the visible absorbance spectrum and thus coloration tints which are chestnut brown or dark gray.

The sensitivity, as well as the height and the area of their $\lambda_{max}$ peaks in the visible, attain satisfactory values.

These compounds are also perfectly stable and compatible with support matrixes made of organic polymer or of mineral material, both in a form included in the matrix and in the form of a coating.

In solution or in a polymer matrix, the compounds according to the invention are colorless or slightly colored in the initial state and they rapidly develop an intense coloration under UV light (365 nm) or a light source of the solar type. Finally, they quickly recover their initial color when the irradiation stops.

The compounds of the invention can be obtained by the condensation of an indoline derivative substituted with a polycyclic $R^1$ group and an aromatic nitroso alcohol derivative such as those described, for example, in U.S. Pat. Nos. 3,578,602; 4,634,767; 4,913,544 and European Patent No. 600,669. This reaction can take place in solvents such as ethanol, toluene or dichloroethane.

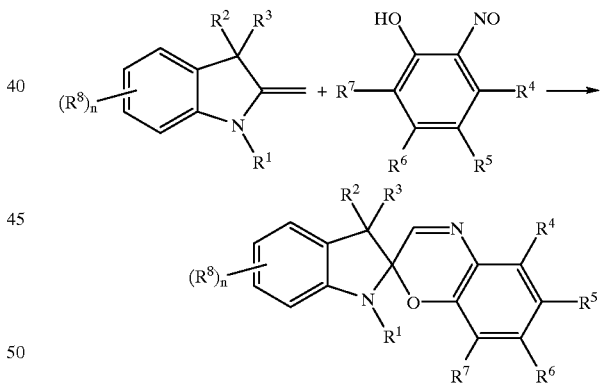

The indoline derivatives are obtained by methods which are adapted from the literature.

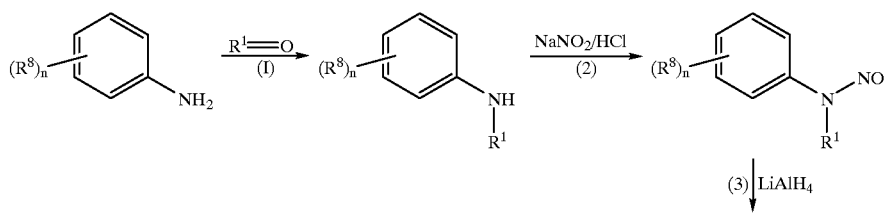

-continued

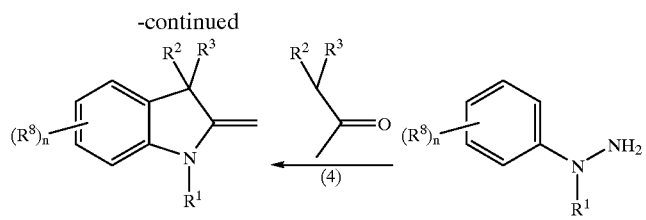

Step 1 is carried out according to a procedure described in Katritzky et al., Tetrahedron 47:2683, 1991. The nitrosation of the amine (step 2) is carried out by a reaction with sodium nitrite-hydrochloric acid and the reduction of the nitroso derivative (step 3) is carried out by the reaction of LiAlH$_4$ in THF (Fridman et al., Russian Chemical Reviews 40(1):34.197. The last step of the synthesis (4) is carried out by reacting hydrazine with the appropriate ketone in an acidic medium, for example, hydrochloric acid/ethanol or acetic acid (for a general review of this reaction one can consult Robinson "Fischer indole synthesis," Wiley-Interscience, 1982.

In the case of applications of compounds according to the present invention, it should be noted that they can be used as a photochromic material which is dispersed in the superficial part or in the composition of a polymer or mineral matrix. They can also be used in solution.

A photochromic solution can be obtained by dissolving the compound in an organic solvent such as toluene, dichloromethane, tetrahydrofuran or ethanol. The solutions obtained are, in general, colorless and transparent. When exposed to sunlight, they developed a strong coloration and their colorless state returns when they are placed in a zone with less exposure to sunlight or, in other works, when they are no longer exposed to UV radiation. In general, it is sufficient to use a very small concentration of product (on the order of 0.01–5%) to obtain an intense coloration.

The most intense applications are those in which the photochrome is dispersed uniformly within or on the surface of a polymer, copolymer or mixture of polymers. A great variety of methods of implementation can be considered. Those known to persons skilled in the art include, for example, diffusion in the (co)polymer, from a suspension or solution of the photochrome, in a silicone oil, in an aliphatic or aromatic hydrocarbon, in a glycol, or from another polymer matrix. The diffusion is routinely carried out at a temperature of 50–200° C. for a duration of 15 min to several hours, depending on the nature of the polymer matrix.

Another implementation technique consists in mixing the photochrome in a formulation of polymerizable substances, in depositing this mixture on a surface or in a mold and in then conducting the polymerization.

These implementation techniques and others are described in the article by Crano et al. "Spiroxazines and their use in photochromic lenses" published by Applied Photochromic Polymer Systems, Published by Blackie and Son Ltd., 1992.

According to a variant of the invention, it is also possible to consider grafting the photochromes onto (co)polymers. Thus, another object of the invention consists of (co) polymers to which at least one of the photochromes described above has been grafted.

Examples of preferred polymer materials for the optical applications of the photochromic compounds according to the invention include the following products:

alkyl, cycloalkyl, aryl or arylalkyl (mono, di, tri or tetra) polyacrylate of polymethylacrylate, optionally halogenated or comprising at least one ether and/or ester and/or carbonate and/or carbamate and/or thiocarbamate and/or urea and/or amide group, polystyrene, polycarbonate (e.g., bisphenol-A polycarbonate, allyl diethylene glycol polycarbonate), polyepoxy, polyurethane, polythiourethane, polysiloxane, polyacrylonitrile, polyamide, aliphatic or aromatic polyester, vinyl polymers, cellulose acetate, cellulose triacetate, cellulose acetate-propionate or polyvinylbutyral, copolymers of two or several types of monomer or mixtures of polymers mentioned above, preferably polycarbonate-polyurethane, poly)meth)acrylate-polyurethane, polystyrene-poly(meth)acrylate or polystyrene-polyacrylonitrile, advantageously a mixture of polyester and of polycarbonate or of poly(meth) acrylate.

The quantity of photchrome used depends on the desired degree of darkening. Usually a quantity of 0.001–20 wt % is used.

The photochromic compounds according to the invention can be used alone or in a mixture with other products to form a composition which can be in solid or liquid form, for example, in a solution or in a dispersion, as already indicated above. These compositions, which constitute another object of the invention, can thus comprise the compounds (I), (I') of the invention and other complementary photochromic compounds which allow the obtention of dark colorations, for example, gray or brown, which are desired by the public in applications such as eyeglasses or shades. These complementary photochromic compounds have an $\lambda_{max}$ and an absorbance area surface in the visible such that, after association with the compounds of the invention, an absorbance spectrum is obtained which covers the entire visible spectrum and which imparts the desired tint to the mixture of activated photochromes.

The photochrome(s), which can be combined with the compounds of the invention, is/are those known to a person skilled in the art and described in the literature, for example, chromenes (U.S. Pat. Nos. 3,567,605; 5,238,981; World Patent No. 9,422,850; European Patent No. 0,562,915), spiropyrans or naphthospyropans [sic; naphthospiropyrans] (U.S. Pat. No. 5,238,981) and spiroxazines (J. C. Crano et al., "Applied Photochromic Polymer Systems, " Publisher, Blackie & Son Ltd., 1992, Chapter 2).

These compositions according to the invention can also comprise:

nonphotochromic dyes which allow an adjustment of the tint, and/or one or more stabilizers, such as, for example, an antioxidant, and/or one or more anti-UV agents, and/or one or more antiradical compounds, and/or one or more deactivators of photochemical excitation states.

These additives can allow an improvement of the durability of said compositions.

According to another of its aspects pertaining to the application of the photochromic compounds (I), (I'), the present invention also relates to ophthalmic articles, such as eyeglass or sunshade articles, comprising at least one compound according to the invention and/or at least one (co) polymer formed, at least in part, of recurrent units of type (I), (I') and/or at least one composition comprising the compounds (I), (I') according to the invention, as defined above, and/or at least one matrix, as defined above, made of an organic polymer material or of a mineral material or of a mineral-organic hybrid material incorporating at least one compound of the invention.

In practice, the articles which are more particularly referred to by the present invention are photochromic eyeglass lenses or shades, glare partitions (windows for buildings, for locomotives, automobiles), the optical devices, the decorative articles, the sun protection articles, the storage of data, etc.

The present invention will be understood better in the light of the following examples of photochromic synthesis and validation of compounds (I), (I') and (I"), which it concerns.

EXAMPLES

Synthesis and properties of photochromic compounds (1)–(8) according to the invention (Examples 1–8).

The formulas of compounds (1)–(8) are given below (see Table I).

Example 1: Synthesis of compound (1)

Step 1
Synthesis of 2-norbornylphenylamine

In a 250 mL flask equipped with a Dean-Start separator, the following mixture is brought to reflux: 9.3 g of aniline, 12.1 g 2-norbornanone, 13.2 g benzotriazole and 120 mL xylene. After 16 h, the mixture is reduced to dryness, then it is solubilized in 300 mL methanol, and the product is reduced with 6 g $NaBH_4$ at 50° C. for 1 h. The mixture is then poured into 200 mL water and the organic product is extracted with 3×100 mL toluene. The organic phase is recovered, dried over magnesium sulfate, and then reduced to dryness. In this manner, 20 g of the desired amine are produced.

Step 2
Synthesis of 1-(2-norbornylphenyl)-1-phenylhydrazine

The amine from the preceding step (20 g) is suspended in 100 mL of hydrochloric acid (1N), and then the mixture is maintained at 0° C. with stirring. An aqueous solution of $NaNO_2$ (7 g in 20 mL of water) is then added to the mixture in small portions. The temperature is then allowed to rise to the ambient temperature, and the nitroso derivative is extracted with 3×100 mL toluene. After evaporation of the solvent, 26 g of product are recovered. This product is then added slowly and in small portions into tetrahydrofuran (200 mL) containing 7 g $LiAlH_4$ and, then the mixture is maintained at ambient temperature for 1 h. Subsequently, the mixture is cooled to 0° C., and then the excess hydride is neutralized with an aqueous sodium hydroxide solution. Next, 30 g $Na_2SO_4$ are added, and the organic phase is recovered by filtration and reduced to dryness. In this manner 21 g of the desired hydrazine are produced.

Step 3 Synthesis of the 2-methyleneindoline derivative.

In a 100 mL flask, 21 g hydrazine from the preceding step and 8.6 g 3-methyl-2-butanone in 100 mL ethanol containing 2 mL acetic acid at 50° C. are reacted. Then 15 mL of concentrated hydrochloric acid are added and brought to reflux for 30 min. The mixture is then neutralized with sodium hydroxide to pH 10 and the indole derivative is extracted with 3×100 mL isopropyl ether. After evaporation of the solvent, 17 g of the desired product are prepared.

Step 4
Synthesis of spiroxazine (1)

The product from the preceding step (3 g) and 1.5 g 1-nitroso-2-naphthol are dissolved in 50 mL of absolute ethanol, and then the mixture is heated at 60° C. for 1 h. The mixture is then cooled to 0° C. After 30 min, the precipitated product is recovered by filtration, and washed with ethanol (20 mL). The solid is then recrystallized in ethanol. 820 mg of the desired product are isolated after filtration. Its structure is confirmed by NMR spectroscopy and the latter reveals, in addition, the existence of two isomers (because of the end- or exo- position of the nitrogen on the norbornyl ring):

Example 2: Synthesis of compound (2)

The product from step 3 of Example 1 (2.6 g) and 1.9 g 1-nitroso-2,7-dihydroxynaphthalene are dissolved in 130 mL ethanol, and the mixture is brought to reflux for 5 h. The spiroxazine which is hydroxylated in the 9' position is isolated from the reaction mixture by chromatography on a silica column with a toluene/methanol mixture (9/1) as eluant. The methylation of the product is then carried out with dimethyl sulfate in acetone, in the presence of potassium carbonate and at 30° C. for 4 h. 1.8 g spiroxazine (2) are isolated after purification by chromatography on a silica column with a toluene/heptane (1/1) mixture as eluent. Its structure is confirmed by NMR spectroscopy.

Example 3: synthesis of compound (3)

Compound (3) is synthesized in a similar manner to that of Example 1. In Example 1, 3,4-dimethylaniline is used instead of aniline. Steps 2 and 3 lead to the indoline derivative, which is then condensed with 1-nitroso-2-naphthol to yield spiroxazine 3. It is purified as above by chromatography on a silica column. Its structure is confirmed by NMR spectroscopy. The latter reveals the existence of a mixture of two dimethyl isomers (position 4,5 and 5,6 on the phenyl ring of the indole).

Example 4: Synthesis of compound (4)

Compound 4 is synthesized in a manner similar to that of Example 2. In step 4, the indoline derivative prepared in Example 3 and 1-nitroso-2,7-dihydroxynaphthalene are used. the intermediate obtained is then methylated with dimethyl sulfate in acetone in the presence of potassium carbonate. The spiroxazine is purified as above by column chromatography on silica. Its structure is confirmed by NMR spectroscopy.

Example 5: Synthesis of compound (5)

This compound is synthesized in a manner similar to that of Example 1, using as the starting product camphor instead of 2-norbornanone in step 1 of the synthesis.

Example 6: synthesis of compound (6)

This compound is synthesized in a manner similar to that of Example 1, using as the starting product 3,4-dimethylaniline and camphor in step 1 of the synthesis.

Example 7: Synthesis of compound (7)

This compound is synthesized in a manner similar to that of the preceding example with 3,5-dimethylaniline instead of 3,4-dimethylaniline in step 1 of the synthesis.

Example 8: Synthesis of compound (8)

This compound is synthesized in a manner similar to that of the Example 3 with 3-methyl-2-pentanone instead of 3-methyl-2-butanone in step 3 of the synthesis.

Applications

Example 9: Incorporation of compounds (1) through (8) in a polyacrylate

General procedure: 10 mg of each one of compounds (1) through (8) are dissolved in tetraethoxylated bisphenol A dimethyl methacrylate, marketed under the name DIACRYL 121 by the company AKZO) and also containing 40 mg 2',2'-azobis(2-methylbutyronitrile). The solution is then degassed, rendered inert with argon and then poured into a glass lens mold having a diameter of 8 cm and a thickness of 2 mm. The mold is then placed in an oven at 70° C. for 12 h. After removal from the mold, a transparent and rigid lens is obtained. When exposed to solar radiation, the glass quickly develops an intense blue coloration and it becomes colorless again in darkness. The photochromic characteristics are given in Table I below. For comparison, the characteristics of compounds C1, C2, C3, C4 and C5 of the prior art are also given in Table I below.

Table I

Legends

- $\lambda_{max}$ measured in D121 in a thickness of 2 mm with exposure to a xenon lamp, 60,000 lx, at 22° C.,
- T0=initial transmission (inactivated state) measured at $\lambda_{max}$,
- TD15=transmission after 15 min of exposure measured at $\lambda_{max}$,
- IOD=Induced optical density {log(T0/TD15)},
- R5=% of recovery of the initial transmission after 5 min of decoloration,
- $(Y0/Y15)_{0h}$=initial integrated transmission and transmission after 15 min of exposure, respectively, and before ageing,
- $Y0/YD15)_{300h}$=initial integrated transmission and transmission after 15 min of exposure after 300 h of ageing under an exposure to 60,000 lx.

TABLE I

| Compound | structure | Proportion % | $\lambda_{max}$ nm | T0 % | TD15 % | DOI | R5 % | $(Y0/YD15)_{0h}$ $(Y0/YD15)_{300h}$ |
|---|---|---|---|---|---|---|---|---|
| Ex. 1 | 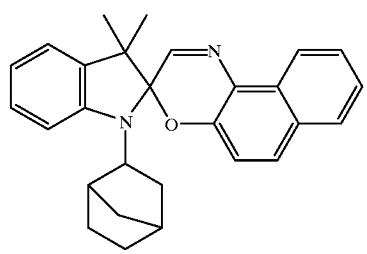 | 0.1 | 612 | 90 | 35 | 0.41 | 82 | 90/57 89/56 |
| Ex. 2 | 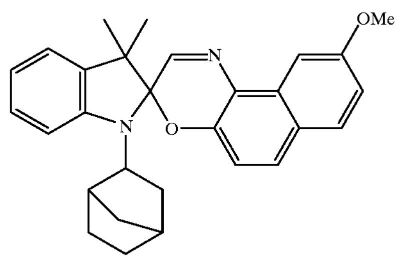 | 0.1 | 608 | 89 | 23 | 0.59 | 77 | 89/42 89/40 |
| Ex. 3 | 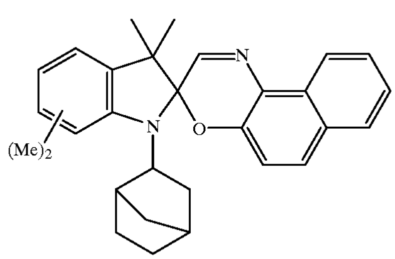 | 0.1 | 624 | 91 | 9 | 0.99 | 65 | 90/39 87/38 |

TABLE I-continued
| Compound | structure | Proportion % | $\lambda_{max}$ nm | T0 % | TD15 % | DOI | R5 % | (Y0/YD15)$_{0h}$ (Y0/YD15)$_{300h}$ |
|---|---|---|---|---|---|---|---|---|
| Ex. 4 | 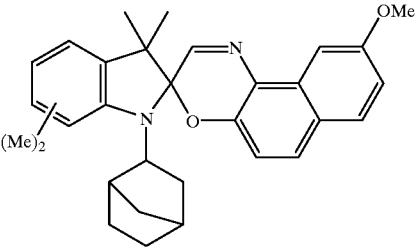 | 0.1 | 618 | 91 | 8 | 1.08 | 67 | 91/32<br>88/28 |
| Ex. 5 | 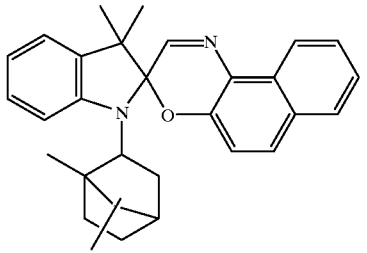 | 0.1 | 616 | 88 | 15 | 0.77 | 67 | |
| Ex. 6 | 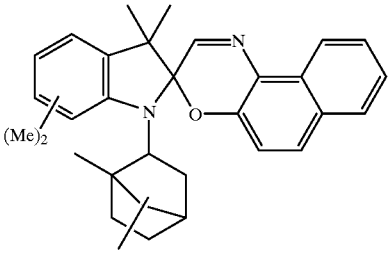 | 0.1 | 624 | 88 | 0.5 | 2.25 | 35 | 88/18<br>86/24 |
| Ex. 7 | 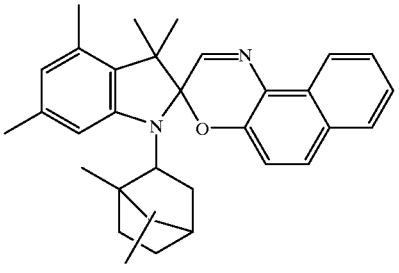 | 0.1 | 616 | 89 | 1.0 | 1.95 | 22 | 89/17<br>80/22 |
| Ex. 8 | 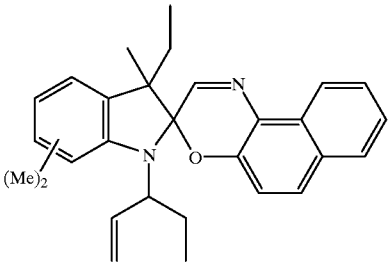 | 0.1 | 622 | 89 | 2.3 | 1.59 | 36 | 89/26<br>87/29 |

TABLE I-continued

| Compound | structure | Proportion % | $\lambda_{max}$ nm | T0 % | TD15 % | DOI | R5 % | (Y0/YD15)$_{0h}$ (Y0/YD15)$_{300h}$ |
|---|---|---|---|---|---|---|---|---|
| C1 | 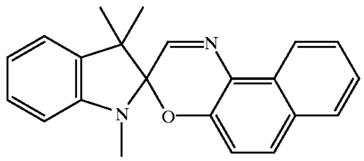 | 0.1 | 604 | 90 | 39 | 0.36 | 83 | — |
| C2 | 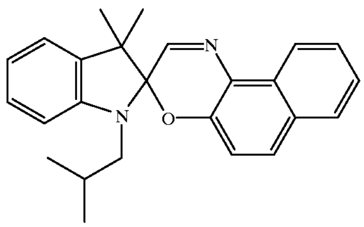 | 0.1 | 610 | 86 | 22 | 0.59 | 74 | 86/44<br>86/43 |
| C3 | 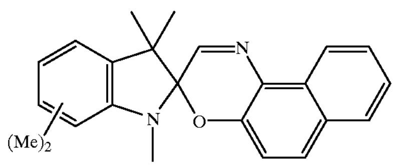 | 0.1 | 616 | 86 | 18 | 0.69 | 68 | — |
| C4 | 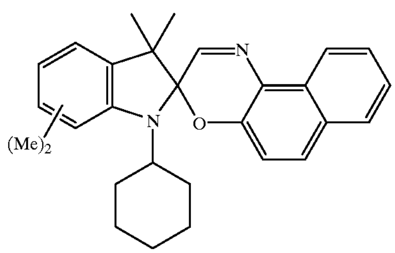 | 0.1 | 624 | 91 | 17 | 0.73 | 70 | 91/48<br>90/40 |
| C5 | 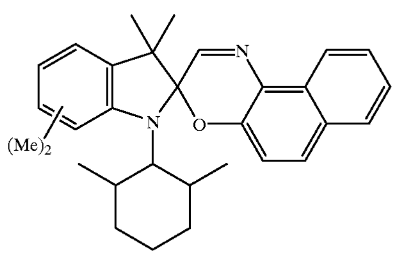 | 0.1 | 620 | 81 | 19 | 0.53 | 63 | 85/48<br>83/47 |

A comparison of the properties of Examples 1, 2 and 5 and of Comparative Examples $C_1$ and $C_2$, on the one hand, and Examples 3, 4 and 6 and Comparative Examples $C_3$–$C_5$, on the other hand, show that the compounds of the prior art with similar structure but without the polycyclic group according to the invention do not possess the advantageous combination of properties sought. In particular, it can be observed that the compounds of the invention have a better compromise between low initial coloration and strong induced optical density, and are photochemically very stable with little or no loss of colorability or decrease of the initial transmission.

I claim:

1. Photochromic compounds having the following general formula (I):

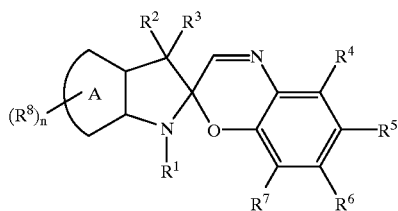

(I)

in which,

R¹ is a polycyclic group formed by at least one alicyclic group linked to bridged or condensed with at least one other aliphatic and/or aromatic ring, where the rings can optionally contain at least one heteroatom and at least one unsaturation, R² and R³ are identical or different and represent an alkyl group, straight or branched, of 1–12 carbon atoms, an alkenyl group, an alkynyl group, an aryl group, an alkylaryl group, or a cycloalkyl group, or R² and R³ combine to form a carbocyclic or heterocyclic group having 5 to 10 atoms, R⁴, R⁵, R⁶, and R⁷ are identical or different and represent:
hydrogen,
an alkyl group, a cycloalkyl group, an alkenyl group, an alkynyl group, an aryl group, a heteroaryl group, an aryloxy group, or an aralkyl group, said group being optionally halogenated,
a halogen,
OR, SR, —OCOR, or —COOR, wherein R is H, alkyl and/or cycloalkyl and/or aryl,
a (poly)ether, a (poly)amide, a (poly)carbonate, a (poly)carbamate, a (poly)urea, or a (poly)ester,
* an amino radical which gives rise, once it is bound in (I), to a primary, secondary, or tertiary amine, said amine being alkyl, aryl, or aralkyl, mono- or disubstituted, or
* an aminocyclic radical containing, optionally, one or more heteroatoms, or
an election withdrawing group,
where at least two of the radicals R⁴, R⁵, R⁶, and R⁷ can optionally form an assembly of at least one aromatic ring having 5 or 6 members or aliphatic ring having 5 to 7 members, said ring(s) comprising, optionally, at least one heteroatom, so as to form at least one heterocyclic ring, the latter being optionally substituted by one or more radicals, identical or different, and having the same definition as given above for R⁴ to R⁷, A represents an aromatic or heteroaromatic ring optionally substituted by one or more radicals R⁸, which are identical or different and which have the same definition as given above for R⁴ to R⁷, and n is a whole number, and, when n≧2, two of the radicals R⁶ can optionally combine to form at least one aromatic or heteroaromatic ring.

2. Compounds according to claim 1, characterized in that the polycyclic group R¹ is a bicyclic group.

3. Compounds according to claim 2, characterized in that the bicyclic group is asymmetric.

4. Compounds according to claim 1, characterized in that R¹ is selected from the following groups:

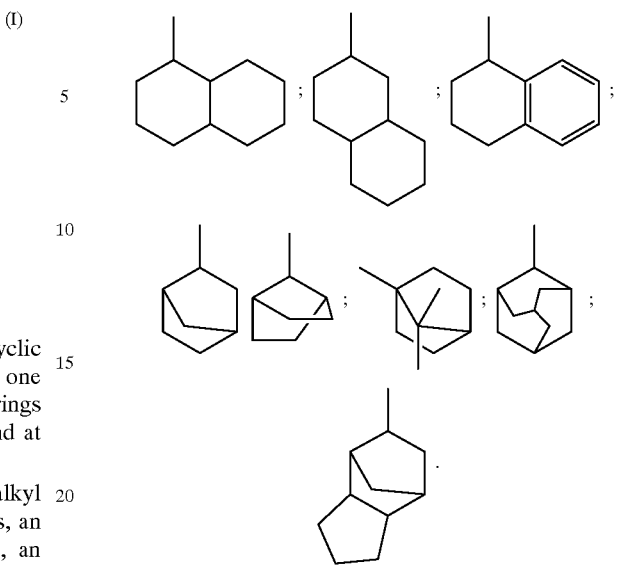

5. Compounds according to claim 1, characterized in that the group R¹ is a substituted or unsubstituted norbornyl group.

6. Photochromic compounds having the following general formula (I'):

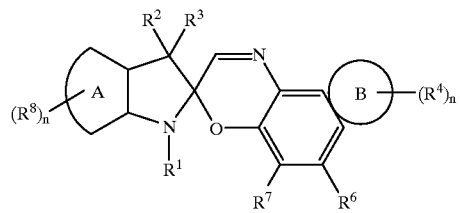

(I')

in which,

R¹ is a polycyclic group formed by at least one alicyclic group linked to ridged or condensed with at least one other aliphatic and/or aromatic ring, where the rings can optionally contain at least one heteroatom and at least on unsaturation, R² and R³ are identical or different and represent an alkyl group, straight or branched, of 1–12 carbon atoms, an alkenyl group, an alkynyl group, an aryl group, an alkylaryl group, or a cycloalkyl group, or R² and R³ combine to form a carbocyclic or heterocyclic group having 5 to 10 atoms, R⁴, R⁶, and R⁷ are identical or different and represent:
hydrogen,
an alkyl group, a cycloalkyl group, an alkenyl group, an alkynyl group, an aryl group, a heteroaryl group, an aryloxy group, or an aralkyl group, said group being optionally halogenated,
a halogen,
OR, SR, —OCOR, or —COOR, wherein R is H, alkyl and/or cycloaklyl and/or aryl,
a (poly)ether, a (poly)amide, a (poly)carbonate, a (poly)carbamate, a (poly)urea, or a (poly)ester,
* an amino radical which gives rise, once it is bound in (I'), to a primary, secondary, or tertiary amine, said amine being alkyl, aryl, or aralkyl, mono- or disubstituted, or

* an aminocyclic radical containing, optionally, one or more heteroatoms, or an election withdrawing group, where the radicals $R^6$ $R^7$ can optionally form an assembly of at least one aromatic ring having 5 or 6 members or aliphatic ring having 5 to 7 members, said ring(s) comprising, optionally, at least one heteroatom, so as to form at least one heterocyclic ring, the later being optionally substituted by one or more radicals, identical or different, and having the same definition as given above for $R^4$, $R^5$, and $R^7$, A represents an aromatic or heteroaromatic ring optionally substituted by one or more radicals $R^8$, which are identical or different and which have the same definition as given above for $R^4$, $R^5$, and $R^7$, n is a whole number, and, when n≧2, two of the radicals $R^8$ can optionally combine to form at least one aromatic or heteroaromatic ring, and B is an aromatic or aliphatic ring having 5 to 7 members.

7. Photochromic compounds according to claim 1, characterized in that they have the following general formula (I"):

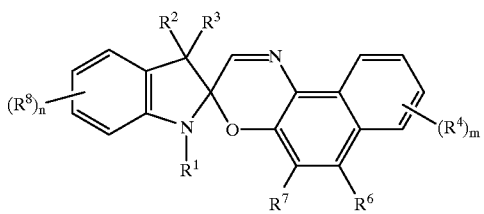

in which $R^1$–$R^4$ and $R^6$–$R^8$ are defined as in claim 1, and n and m have values from 0 to 4.

8. Compounds according to claim 1, characterized in that the groups $R^1$–$R^9$ of formula (I) according to the invention comprise and/or form at least one reactive polymerization and/or cross-linking group selected from the following: alkenyl, methacroyl, acroyl, acryloxyalkyl, methacryloxalkyl, and epoxy.

9. Compounds according to claim 1, characterized in that they present the following formula:

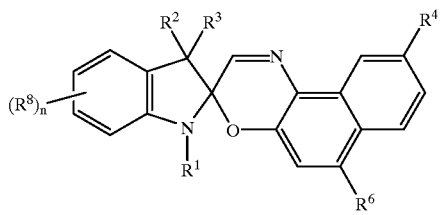

where N—$R^1$ is selected from the following group of formulae:

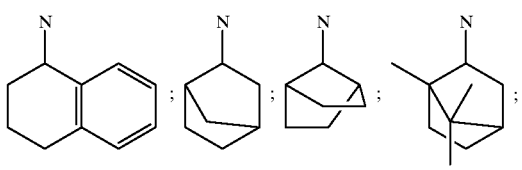

-continued

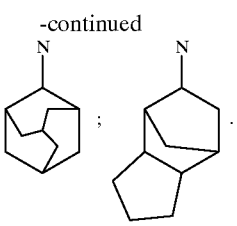

10. (Co)polymer and/or crosslinkage, obtained by the polymerization and/or crosslinking of at least one monomer consisting of at least one photochromic compound according to claim 8.

11. (Co)polymer, characterized in that it is grafted with at least one photochromic compound according to claim 1.

12. Photochromic composition, characterized in that it comprises:

at least one compound according to claim 1, and optionally at least one other photochromic compound and/or at least one dye and/or at least one stabilizer.

13. (Co)polymer matrix, characterized in that it comprises:

at least one compound according claim 1.

14. Matrix according to claim 13, characterized in that the (co)polymer is selected from the following list:

alkyl, cycloaklyl, aryl, or arylalkyl (mono, di, tri, or tetra) polyacrylate or polymethacrylate optionally halogenated or comprising at least one ether and/or ester and/or carbonate and/or carbamate and/or thiocarbamate and/or urea and/or amide group, polystyrene, polycarbonate, polyepoxy, polyurethane, polythiourethane, polysiloxane, polyacrylonitrile, polyamide, aliphatic or aromatic polyester, polyvinyl acetate, cellulose acetate, cellulose triacetate, cellulose acetate propionate, or polyvinylbutyral, and copolymers of two or more types of monomer or mixtures of the monomers indicated above.

15. Ophthalmic or solar article comprising:

at least one compound according to claim 1.

16. Article according to claim 15, characterized in that it consists of a lens.

17. Glass partition and/or optical device comprising:

at least one compound according to claim 1.

18. Photochromic compound according to claim 6, characterized in that B comprises a heteroatom which is substituted by one or more radicals.

19. Photochromic compound according to claim 18, characterized in that the radicals have the same definition as $R^4$ to $R^7$.

20. (Co)polymer, characterized in that it is grafted with at least one photochromic compound according to claim 6.

21. Photochromic composition, characterized in that it comprises:

at least one compound according to claim 6, and optionally at least one other photochromic compound and/or at least one dye and/or at least one stabilizer.

22. (Co)polymer matrix, characterized in that it comprises:

at least one compound according to claim 6.

23. Matrix according to claim 22, characterized in that the (co)polymer is selected from the following list:

alkyl, cycloaklyl, aryl, or arylalkyl (mono, di, tri, or tetra) polyacrylate or polymethacrylate optionally halogenated or comprising at least one ether and/or ester and/or carbonate and/or carbamate and/or thiocarbamate and/or urea and/or amide group, polystyrene, polycarbonate, polyepoxy, polyurethane, polythiourethane, polysiloxane, polyacrylonitrile, polyamide, aliphatic or aromatic polyester, polyvinyl acetate, cellulose acetate, cellulose triacetate, cellulose acetate propionate, or polyvinylbutyral, and copolymers of two or more types of monomer or mixtures of the monomers indicated above.

24. Ophthalmic or solar article comprising:

at least one compound according to claim 6.

25. Article according to claim 24, characterized in that it consists of a lens.

26. Glass partition and/or optical device comprising:

at least one compound according to claim 6.

27. Photochromic composition, characterized in that it comprises:

at least one (co)polymer according to claim 10 and optionally at least one other photochromic compound and/or at least one dye and/or at least one stabilizer.

28. Photochromic composition, characterized in that it comprises:

at least one (co)polymer according to claim 11 and optionally at least one other photochromic compound and/or at least one dye and/or at least one stabilizer.

29. Photochromic composition, characterized in that it comprises:

at least one (co)polymer according to claim 20 and optionally at least one other photochromic compound and/or at least one dye and/or at least one stabilizer.

30. (Co)polymer matrix, characterized in that it comprises:

at least one (co)polymer according to claim 10.

31. Matrix according to claim 30, characterized in that the (co)polymer is selected from the following list:

alkyl, cycloalkyl, aryl, or arylalkyl (mono, di, tri, or tetra) polyacrylate or polymethacrylate optionally halogenated or comprising at least one ether and/or ester and/or carbonate and/or carbamate and/or thiocarbamate and/or urea and/or amide group, polystyrene, polycarbonate, polyepoxy, polyurethane, polythiourethane, polysiloxane, polyacrylonitrile, polyamide, aliphatic or aromatic polyester, polyvinyl acetate, cellulose acetate, cellulose triacetate, cellulose acetate propionate, or polyvinylbutyral, and copolymers of two or more types of monomer or mixtures of the monomers indicated above.

32. (Co)polymer matrix, characterized in that it comprises:

at least one (co)polymer according to claim 11.

33. Matrix according to claim 32, characterized in that the (co)polymer is selected from the following list:

alkyl, cycloalkyl, aryl, or arylalkyl (mono, di, tri, or tetra) polyacrylate or polymethacrylate optionally halogenated or comprising at least one ether and/or ester and/or carbonate and/or carbamate and/or thiocarbamate and/or urea and/or amide group, polystyrene, polycarbonate, polyepoxy, polyurethane, polythiourethane, polysiloxane, polyacrylonitrile, polyamide, aliphatic or aromatic polyester, polyvinyl acetate, cellulose acetate, cellulose triacetate, cellulose acetate propionate, or polyvinylbutyral, and copolymers of two or more types of monomer or mixtures of the monomers indicated above.

34. (Co)polymer matrix, characterized in that it comprises:

at least one (co)polymer according to claim 20.

35. Matrix according to claim 34, characterized in that the (co)polymer is selected from the following list:

alkyl, cycloaklyl, aryl, or arylalkyl (mono, di, tri, or tetra) polyacrylate or polymethacrylate optionally halogenated or comprising at least one ether and/or ester and/or carbonate and/or carbamate and/or thiocarbamate and/or urea and/or amide group, polystyrene, polycarbonate, polyepoxy, polyurethane, polythiourethane, polysiloxane, polyacrylonitrile, polyamide, aliphatic or aromatic polyester, polyvinyl acetate, cellulose acetate, cellulose triacetate, cellulose acetate propionate, or polyvinylbutyral, and copolymers of two or more types of monomer or mixtures of the monomers indicated above.

36. Ophthalmic or solar article comprising:

at least one (co)polymer according to claim 10.

37. Article according to claim 36, characterized in that it consists of a lens.

38. Ophthalmic or solar article comprising:

at least one (co)polymer according to claim 11.

39. Article according to claim 38, characterized in that it consists of a lens.

40. Ophthalmic or solar article comprising:

at least one (co)polymer according to claim 20.

41. Article according to claim 40, characterized in that it consists of a lens.

42. Glass partition and/or optical device comprising:

at least one (co)polymer according to claim 10.

43. Glass partition and/or optical device comprising:

at least one (co)polymer according to claim 11.

44. Glass partition and/or optical device comprising:

at least one (co)polymer according to claim 20.

* * * * *